United States Patent [19]

Noishiki et al.

[11] Patent Number: 4,690,973

[45] Date of Patent: Sep. 1, 1987

[54] PRODUCTION PROCESS OF AN ANTITHROMBOGENIC AND ANTIADHESIVE MATERIAL FOR MEDICAL USE

[75] Inventors: Yasuharu Noishiki, Tottori; Kazuhiko Kodaira, Mitaka; Masayasu Furuse, Sagamihara; Teruo Miyata, Tokyo; Takeaki Miyamoto, Nagaokakyo; Hiraku Ito, Kyoto, all of Japan

[73] Assignee: Koken Company Limited, Tokyo, Japan

[21] Appl. No.: 885,782

[22] Filed: Jul. 15, 1986

[30] Foreign Application Priority Data

Jul. 29, 1985 [JP] Japan ................................. 60-165990

[51] Int. Cl.$^4$ .................... C08H 1/06; C08L 89/04; C08L 89/06
[52] U.S. Cl. ............................. 525/54.1; 128/334 R; 128/335.5; 128/DIG. 8; 514/21; 530/356
[58] Field of Search .................. 530/356; 525/54.1; 128/334 R, 335.5, DIG. 8; 514/21

[56] References Cited

U.S. PATENT DOCUMENTS

| | | | |
|---|---|---|---|
| 4,233,360 | 11/1980 | Luck et al. | 530/356 X |
| 4,238,480 | 12/1980 | Sawyer | 530/356 X |
| 4,280,954 | 7/1981 | Yannas et al. | 530/356 |
| 4,451,397 | 5/1984 | Huc et al. | 530/356 X |

FOREIGN PATENT DOCUMENTS 0092414  10/1983  European Pat. Off. .

*Primary Examiner*—Howard E. Schain
*Attorney, Agent, or Firm*—Sherman and Shalloway

[57] ABSTRACT

This invention concerns a production process of an antithrombogenic and antiadhesive material which can favorably be used as artificial blood vessels, artificial valves, grafting patches for cardiovascular organs, artificial heart catheters and so on. The gist of this invention is constructed substantially of subjecting glycidyltrialkylammonium halide such as glycidyltrimethylammonium chloride to the reaction with a material comprising pure collagen or collagen and other components like mucopolysaccharide in order to introduce a cationic quaternary functional group in collagen molecules of the material and then subjecting heparin to the ionic combination with the cationic functional group introduced. Meanwhile, in advance of the above chemical treatment, the material is prepared from dog's blood vessel by removing proteins except collagen, from cow's Achilles tendon by crushing into powder, from human amnion by rinsing in distilled water or from polyester knit tube by coating its inside with powdered collagen, for example.

4 Claims, No Drawings

PRODUCTION PROCESS OF AN ANTITHROMBOGENIC AND ANTIADHESIVE MATERIAL FOR MEDICAL USE

FIELD OF THE INVENTION

This invention concerns a production process of an antithrombogenic and antiadhesive material for medical use. More particularly, this invention concerns a production process of an antithrombogenic and antiadhesive material which can favorably be used as artificial blood vessels, artificial valves, grafting patches for cardiovascular organs, artificial heart catheters and so on.

DESCRIPTION OF THE PRIOR ART

Unless artificial blood vessels, artificial valves, artificial hearts or other artificial organs always kept in contact with blood are antithrombogenic, there forms thrombus on their contact area, which surely brings a grave influence to a living body.

Incidentally, collagen is so excellent in the affinity with living cells that it is increasingly used for medical care these days. But it used to be difficult to be employed for artificial blood vessel, etc. because collagen itself is not antithrombogenic. The situation was such that the present inventors made various attempts to impart antithrombogenicity to collagen. As a result, they had filed an application for patent that matured to Japanese laid-open patent publication No. 58-180162, finding a successful way of providing collagen with antithrombogenicity, the gist of which comprises coupling protamine, one of the basic proteins, and collagen with the aid of a cross-linking agent, and then subjecting heparin, an antithrombogenic substance, to the ionic combination with the protamine. However, procedures of the process were more complicated than those of this invention because it needed the basic protein protamine. Moreover, there is a problem in the antigenicity of protamine, which has been another drawback of the antecedent invention.

SUMMARY OF THE INVENTION

Accordingly, the present inventors keenly studied to eliminate the above drawbacks and accomplished the invention, finding a simpler way of giving collagen antithrombogenicity by no use of proteins like protamine. That is, the invention relates to a production process of antithrombogenic and antiadhesive material for medical use, characterized by subjecting glycidyltrialkylammonium halide to the reaction with a material comprising only collagen or collagen and other components in order to introduce a cationic functional group in collagen molecules of said material and then subjecting heparin to the ionic combination with said cationic functional group introduced.

DETAILED DESCRIPTION OF THE INVENTION

The combination of heparin with collagen according to this invention remarkably helps antithrombin III (heparin cofactor) in blood plasma to control the activity of thrombin. Thus, the formation of fibrin from fibrinogen is put under control. Unless fibrinogen gives rise to fibrin like this, the final reaction in the thrombus formation process, which contributes to blood coagulation, does not occur; therefore, antithrombogenicity results therefrom.

Originally, fibrin has such good affinity with living cells that wounds heal along with the restoration of living cells after the formation of fibrin starts in their healing progress. Nevertheless, adhesion of organs to the surrounding tissues sometimes occurs in the healing progress after surgical operations due to the formation of fibrin, which most likely leads to another trouble. In such a case, the employment of an antiadhesive membrane of this invention prevents the formation of fibrin; that is, any types of adhesion do not follow surgical operations. As apparent from this, antithrombogenicity and antiadhesiveness are the same in principle; heparin plays a role of hindering the formation of fibrin from fibrinogen, and this contributes to both antithrombogenicity and antiadhesiveness. Therefore, as long as the process of this invention is employed, an antithrombogenic and antiadhesive material can be provided even in a simple manner.

Meanwhile, the term collagen, as the term is employed herein, denotes atelocollagen after the removal of telopeptide by the use of protease except collagenase, insoluble collagen separated from skin or tendon by purification, gelatine produced by the denaturation of atelocollagen or insoluble collagen and collagen or gelatine derivatives of the above products obtained through chemical modifications, such as acylation and so on. Furthermore, according to this invention, these pure collagens, a mixture of these collagens and mucopolysaccharide, a composite prepared by coating or impregnating a synthetic polymer material with these collagens or a piece of blood vessels, urethrae, pericardia, etc. taken from animals for the sake of medical use are all able to be used; also, these materials may have a form of filament, sponge, film, nonwoven fabric, tube and whatsoever.

Anyway, this invention can be accomplished by the reaction of heparin, which is an acidic mucopolysaccharide, and a cationic quaternary functional group which is introduced in collagen by the previous reaction of the collagen and glycidyltrialkylammonium halide; that is, it is accomplished by the ionic combination of heparin and collagen by means of the mediator glycidyltrialkylammonium halide. The sequence of the reactions can be expressed as follows:

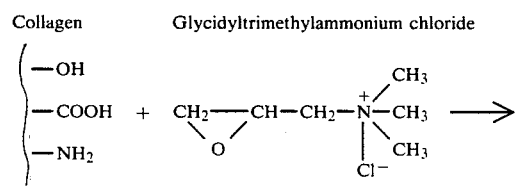

-continued

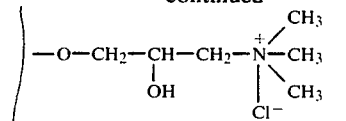

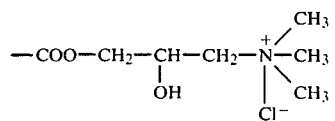 + Heparin⁻

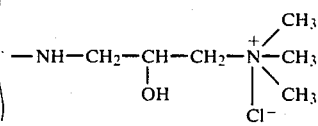

Collagen

The reaction of collagen and gylcidyltrialkylammonium halide can be carried out by putting the latter in a solution of the former or soaking the material comprising collagen in a solution of the latter. Because glycidyltrialkylammonium halide has epoxy radical, it can easily react with amino, carboxy, and hydroxy radicals of collagen; hence, the reaction can be made in relatively mild condition.

Subsequently, collagen provided with a quaternary group by the reaction with glycidyltrialkylammonium halide is soaked in a heparin solution to combine therewith. Concretely, collagen having a quaternary group is soaked in a 0.1–10% heparin solution at ordinary temperature up to 30° C. for 1–5 hours to fulfill the reaction.

Glycidyltrialkylammonium halide employed in this invention is an agent with epoxy radical for causing collagen molecules to have a quaternary group. According to this, various compounds, such as glycidyltrimethylammonium chloride, glycidyltriethylammonium bromide and the like are all included in the same category.

The invention will be understood more readily in referrence with the following examples; however, these examples are not to be construed to limit the scope of the invention.

EXAMPLE 1

A piece of fresh blood vessel (inner diameter; 3 mm and length 6 cm) taken from a dog was steeped in a 0.01% ficin solution of pH 7 at 25° C. for 24 hours. Proteins except collagen were removed by sufficient rising in water. One gram of glycidyltrimethylammonium chloride (GTMAC) was dissolved in 100 ml of water of pH 8. The GTMAC solution was put in the blood vessel and caused to react therewith at 30° C. for 2 hours. After rinsed well in water, the blood vessel was immersed in a 1.5% heparin solution for an hour. An artificial, antithrombogenic blood vessel of this invention was produced after rinsed well in water.

EXAMPLE 2

A piece of Achilles tendon taken from a bovine was crushed, rinsed well in water and dried to obtain tendon collagen therefrom. One gram of the tendon collagen was put in 100 ml of water and pH was adjusted to 3 with 1 N HCl solution. Ten milligrams of hyaluronic acid was added thereto and stirring was made by a homogenizing mixer. The solution was put in a piece of tube (inner diameter: 3 mm and length: 6 cm) knitted with polyester filament with one of its openings closed. While a pneumatic pressure equivalent to 300 mg Hg is being applied, the tube was immersed in a 1% ammonia solution by which the tendon collagen solution inside the tube was neutralized from outside. An hour later, extra collagen solution was removed and a 1% GTMAC solution was put in the tube in replacement. Reaction was made at 30° C. for 2 hours. After thorough rinsing in water, the tube was soaked in a 1% glutaraldehyde solution of pH 9 to give collagen intermolecular cross-links. The tube was rinsed again in water and then soaked in a 1.5% heparin solution so that the inside collagen coupled with GTMAC reacted with heparin. The tube was rinsed in water and freeze-dried. In this way, an artificial, antithrombogenic blood vessel of this invention was produced.

Two sorts of artificial blood vessels produced in Examples 1 and 2 were transplanted to the carotid artery of a dog respectively. Any thrombus was not found there three months thereafter. This means that the retainability of antithrombogenesis was fully kept.

EXAMPLE 3

Ten grams of gelatine were put in 100 ml of water Subsequently, 0.1 g of glycidyltrimethylammonium chloride and 0.15 g of heparin were added thereto. The mixture was heated to 50° C. so that they dissolve well. The solution was put in a piece of tube (inner diameter: 6 mm and length: 10 cm) made out of polyester mesh with one of its openings closed. After thoroughly impregnated with the solution, the tube was soaked in 1% glutaraldehyde solution of pH 7 at 30° C. for 10 hours. It was rinsed in water, immersed in 5% glcerin solution for an hour and dried in the air. An artificial, antithrombogenic blood vessel of this invention was thus produced. It was transplanted to the thoracic aorta of a dog. As a result no thrombus was found inside it.

EXAMPLE 4

The inside of an artificial lung was coated with the mixture of gelatine, glycidyltrimethylammonium chloride and heparin prepared in Example 3. The same process as the one in Example 3 was adopted here to form an antithrombogenic coat. An artificial, antithrombogenic lung of this invention was produced in this way. The lung prevented the adhesion of thrombus and showed no side-effect. The result was very satisfied.

EXAMPLE 5

A piece of human amnion (10 cm × 10 cm) rinsed well in distilled water was immersed in 1 l of 1% (w/w) GTMAC solution of pH 10 at 45° C. for 5 hours to cause reaction. After that, it was rinsed well in water and then immersed in 1% (w/w) heparin solution at 45° C. for an hour to cause reaction. After rinsed well in water, it was kept in 70% ethanol. In this way, a piece of antiadhesive membrane was obtained. With this membrane, an animal experiment was performed. A mongrel adult dog put under general anesthesia was subjected to an abdominal operation. A piece of serous membrane (5 cm × 5 cm) of the large intestine was peeled off, together with longitudinal muscular apparatus thereof. The above antiadhesive membrane was sutured to that portion so as to cover with it. As a result, the portion showed 100% antiadhesiveness.

The first half of the process of this invention comprises subjecting glycidyltrialkylammonium halide to the reaction with a material comprising pure collagen or collagen and other components. Compared with the antecedent invention of the present inventors, which employs protamine for the reaction with collagen, this invention enables more collagen molecules to have a quaternary functional group with less expense and relative case. Therefore, it is also easy to combine plenty of heparin with collagen. Hence, the medical material of this invention, comprising collagen and heparin, shows better affinity with living cells; moreover, heparin has such strong effect in preventing blood coagulation and adhesion that it contributes to antithrombogenicity and antiadhesiveness extending over a long period of time as it is released gradually from the medical material embedded in a living body.

We claim:

1. A production process of an antithrombogenic and antiadhesive material for medical use, characterized by subjecting glycidyltrialkylammonium halide to the reaction with a material comprising only collagen or collagen and other components in order to introduce a cationic functional group in collagen molecules of said material and then subjecting heparin to the ionic combination with said cationic functional group introduced.

2. A production process of an antithrombotic and antiadhesive material for medical use according to claim 1, in which said glycidyltrialkylammonium halide involves glycidyltrimethylammonium chloride.

3. A production process of an antithrombogenic and antiadhesive material for medical use according to claim 1, in which said material comprises collagen and mucopolysaccharide.

4. A production process of an antithrombogenic and antiadhesive material for medical use according to claim 1, in which said material is a composite prepared by coating or impregnating a synthetic polymer material with collagen.

* * * * *